(12) United States Patent
Biskup et al.

(10) Patent No.: US 6,974,880 B2
(45) Date of Patent: Dec. 13, 2005

(54) PROCESS FOR THE MANUFACTURE OF (POLY-)ISOCYANATES IN THE GAS PHASE

(75) Inventors: Klaus Biskup, Leverkusen (DE); Peter Keldenich, Langenfeld (DE); Peter Fuhrmann, Köln (DE); Christian Six, Neuss (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/780,097

(22) Filed: Feb. 17, 2004

(65) Prior Publication Data

US 2004/0167354 A1 Aug. 26, 2004

(30) Foreign Application Priority Data

Feb. 20, 2003 (DE) ................. 103 07 141

(51) Int. Cl.[7] .......................................... C07C 263/00
(52) U.S. Cl. ...................................... 560/347; 560/336
(58) Field of Search ................. 560/347, 336

(56) References Cited

U.S. PATENT DOCUMENTS

| | | | |
|---|---|---|---|
| 4,847,408 A | 7/1989 | Frosch et al. .......... | 560/347 |
| 5,391,683 A | 2/1995 | Joulak et al. .......... | 528/67 |
| 5,449,818 A | 9/1995 | Biskup et al. .......... | 560/347 |
| 5,516,935 A | 5/1996 | Bischof et al. .......... | 560/347 |
| 5,679,839 A | 10/1997 | Armand et al. .......... | 560/347 |
| 5,931,579 A | 8/1999 | Gallus et al. .......... | 366/163.2 |

FOREIGN PATENT DOCUMENTS

| | | |
|---|---|---|
| DE | 300 168 | 5/1992 |
| GB | 2 036 586 | 11/1979 |

*Primary Examiner*—Rachel Gorr
(74) *Attorney, Agent, or Firm*—Joseph C. Gil; John Mrozinski

(57) ABSTRACT

The present invention relates to a process for the manufacture of diisocyanates by phosgenation of the corresponding diamines in which the vaporous diamines, optionally rarefied with an inert gas or with the vapors of an inert solvent, and phosgene are heated separately to temperatures of about 200° C. to about 600° C. and mixed and reacted in a tube reactor characterized in that a number $n \geq 2$ of nozzles directed parallel to the axis of the tube reactor are arranged in the tube reactor, the diamine-containing stream being fed into the tube reactor through the n nozzles and the phosgene stream being fed into the tube reactor through the remaining free space.

12 Claims, 3 Drawing Sheets

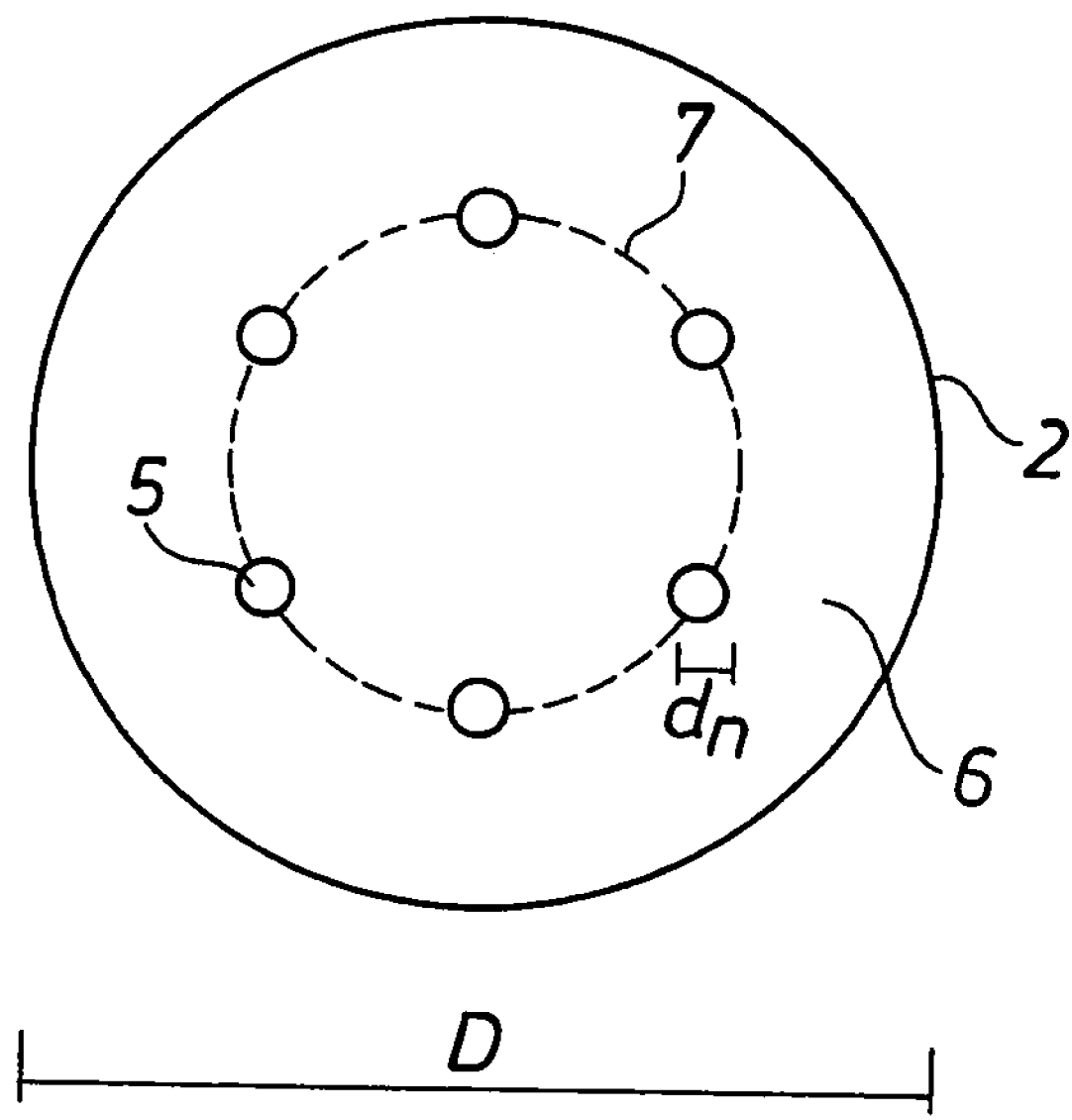

PROCESS FOR THE MANUFACTURE OF (POLY-)ISOCYANATES IN THE GAS PHASE

FIELD OF THE INVENTION

The present invention relates to a continuous process for the manufacture of (poly-)isocyanates by phosgenation of the corresponding (poly-)amines in the gas phase with optimized mixing of the educts.

BACKGROUND OF THE INVENTION

As used herein, (poly-)isocyanates and (poly-)amines are understood to be mono-, di- and polyisocyanates or -amines.

It is known that in gas phase reactions, good mixing of the educts plays an important part in achieving high conversions and selectivities, above all when reacting polyfunctional reactants. An optimum and virtually spontaneous mixing of educts is decisive for the economy of continuous large-scale processes, when a) the reaction of the educts is virtually spontaneous (high reaction speed),
b) one or more educts react with the product at comparably high reaction speeds to produce undesirable di- or oligomeric secondary products, and/or
c) the di- to oligomeric secondary products have a significantly higher boiling point than the educts or the desired product, condense in the reactor at reaction temperature and form deposits (e.g. cracker products, polymeric secondary products) on the reactor walls.

An example is the gas phase phosgenation of aromatic or (cyclo-)-aliphatic polyfunctional amines in a tube reactor. In the continuous process, the educts are normally introduced into a reactor in gas form, as disclosed in various patent applications (e.g. EP-A 699 657, EP-A 676 392, EP-A 593 334, EP-A 570 799, EP-A 289 840).

The reaction of phosgene with (poly)-amine to form (poly-)isocyanate is in competition with the secondary reaction of (poly-)amine and (poly-)isocyanate to form the corresponding urea oligomer. At the conventional reaction temperatures in the tube reactor the urea oligomers of gas phase phosgenation condense on the reactor wall. Improved mixing of the educts phosgene and (poly-)amine, whilst simultaneously avoiding back-flow caused by vortices in the tube reactor, increases the selectivity of (poly-)isocyanate formation and reduces the formation of urea. The quantities of condensation product in the tube reactor, which are deposited on the reactor wall, thus reducing the free tube cross-section and leading to a gradual increase in pressure in the reactor and finally determining the residence time of the process, are thereby reduced.

The reaction partners should be mixed within a time of up to 0.5 seconds to a degree of segregation of $10^{-3}$ The degree of segregation is a measure of the, incompleteness of mixing (EP-A 570 799).

The methods of realizing short mixing times are known in principle. Mixing apparatus with dynamic or static mixing devices is suitable. Static mixers are preferred. There are a number of different possible methods for the construction of static mixing organs, e.g. the use of nozzles, smooth-jet nozzles or Venturi nozzles known from combustion technology.

The disadvantages of many constructions are high pressure-loss or an arrangement that results in insufficiently rapid mixing or leads to re-mixing in the mixing zone or in the reaction chamber. High pressure loss in the mixing apparatus results in an increase in the amount of gaseous educt fed in. Higher pressure loss requires an increased boiling temperature to guarantee adequate pre-pressure. However, particularly with educts containing reactive functional groups, the increased boiling temperature causes thermal damage and therefore increases formation of by-products (yield/selectivity losses). In addition, insufficiently rapid mixing, or re-mixing, leads to an increased residence time of some of the educts and products and consequently to undesirable parallel or secondary reactions. Furthermore, insufficient mixing, particularly in strongly exothermic or endothermic reactions, causes an uneven temperature distribution in the reactor. These so-called "hot spots" and "cold spots" in the reactor result in increased thermal decomposition of the products or undesirably premature condensation of the products. Thermal decomposition products form a solid residue, which is deposited on the reactor walls. In this case the reactor is commonly fitted with an Inliner (reaction tube), which can be changed when it becomes encrusted, thus facilitating reactor cleaning. In the case of a reactor in the form of a cylindrical tube, for example, a simple cylindrically-rolled thin steel sheet of a resistant material is suitable as an Inliner.

The known disadvantages can be minimized if a single, individual nozzle of precisely-specified dimensions is used as the mixing device, which is fitted coaxially into a tube. The tube reactor then has a central nozzle and an annular space between the central nozzle and the wall of the tube reactor. The nozzle thus opens immediately into the reaction chamber (FIG. 1). The educts are mixed immediately after the nozzle outlet. One gaseous educt E1 (phosgene or (poly-)amine) is fed through the central nozzle, the other gaseous educt ((poly-)amine or phosgene) through the annular space between the central nozzle and the wall of the tube reactor into the reaction chamber. In this way, the stream of educt E1 is introduced centrally into the stream of educt E2 and mixed there. The flow rate of E1 must however be greater than the flow rate of E2. Nevertheless, the reactor lifetime that can be achieved with such an arrangement is still not entirely satisfactory.

SUMMARY OF THE INVENTION

The present invention therefore provides a process for the phosgenation of (poly-) amines, with which high yields and high reactor lifetimes can be achieved.

Advantages of the process according to the invention include: shorter mixing times in comparison with a single nozzle (individual nozzles) of the same area of cross-section and as a result of this a reduction in the required residence time in the reactor (advantage for investment costs), a reduction in the formation of by-products and shorter thermal loading of the products thus increasing the relative yield, and the avoidance or reduction of solid deposits on the reactor wall thus prolonging the lifetime of the process.

These and other advantages and benefits of the present invention will be apparent from the Detailed Description of the Invention herein below.

BRIEF DESCRIPTION OF THE FIGURES

The present invention will now be described for purposes of illustration and not limitation in conjunction with the figures, wherein:

FIG. 3 shows a front view of the tube reactor shown in FIG. 2.

DETAILED DESCRIPTION OF THE INVENTION

Figure 1:
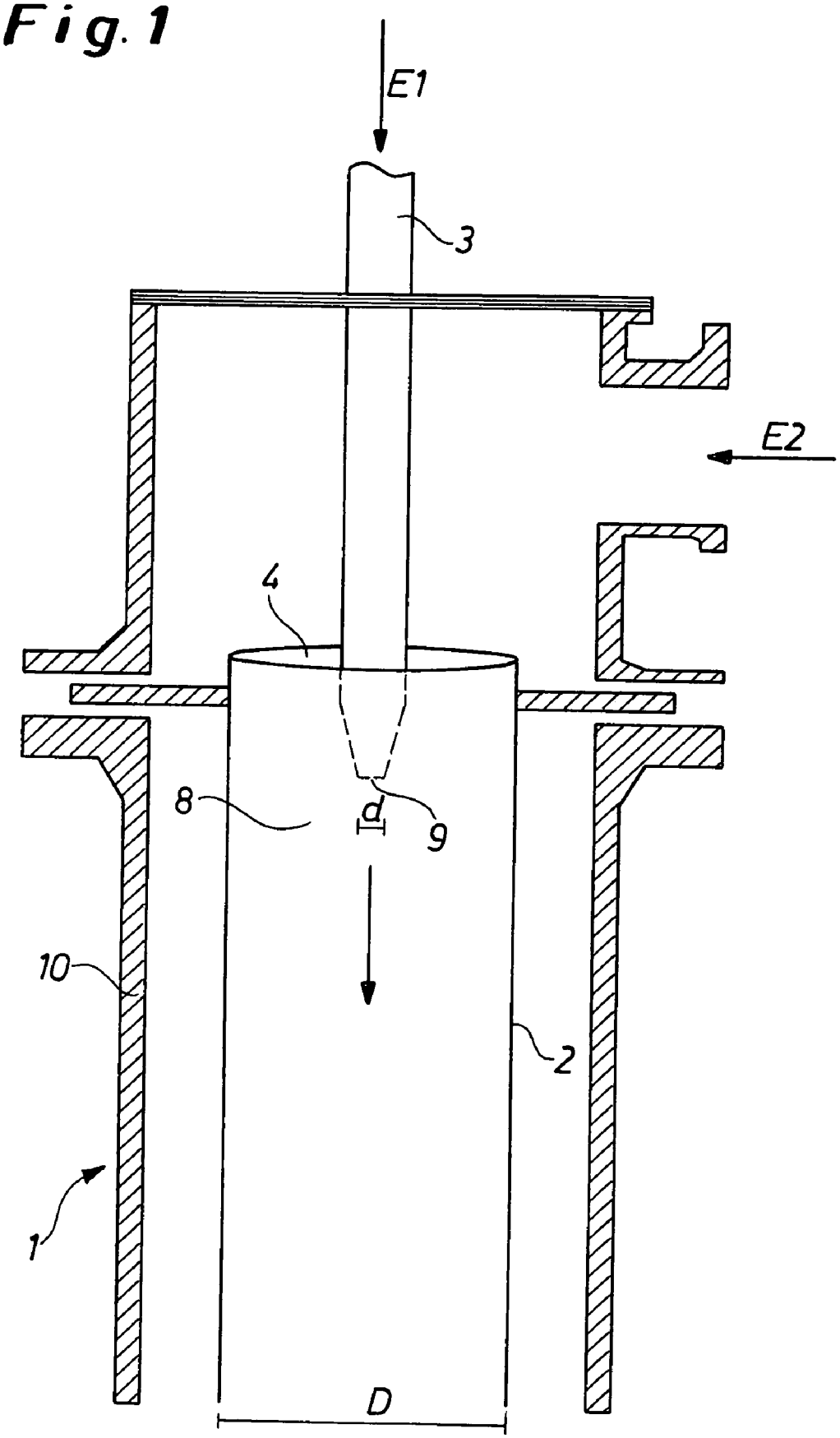
FIG. 1 depicts a tube reactor with a central nozzle.

The present invention will now be described for purposes of illustration and not limitation. Except in the operating examples, or where otherwise indicated, all numbers expressing quantities, percentages and so forth in the specification are to be understood as being modified in all instances by the term "about."

It was found that, for a specific geometry of mixing organs and reactor, it is advantageous for the lifetime of the process and the relative yield, if the free cross-section at the outlet of the single nozzle of educt E1 is divided into several individual nozzles of the same total area (a so-called "multi-nozzle"). For the gas phase reaction of (poly-)amines with phosgene to form (poly-)isocyanates in the process according to the invention, it was found to be more advantageous to feed in the (poly-)amine, for example, through three- to six nozzles arranged in a ring, in a phosgene stream, than through a single nozzle for the (poly-)amine (individual nozzle) of the same area as the multi-nozzle.

The present invention provides a process for the manufacture of a diisocyanate of the formula (I)

in which
R represents a (cyclo-)aliphatic or aromatic hydrocarbon group having up to 15 carbon atoms, provided that at least 2 carbon atoms are arranged between the two NCO groups, by phosgenation of the corresponding vaporous diamine of the formula (II)

in which
R' represents a (cyclo-)aliphatic or aromatic hydrocarbon group having up to 15, preferably 4 to 13 carbon atoms, provided that at lest two carbon atoms are arranged between the two amino groups, in which the vaporous diamines, optionally rarefied with an inert gas or with the vapors of an inert solvent, and phosgene are heated separately to temperatures of 200° C. to 600° C., mixed and reacted in a tube reactor, having a number $n \geq 2$ of nozzles directed parallel to the axis of the tube reactor arranged in the tube reactor, the diamine-containing stream being fed into the tube reactor through the n nozzles and the phosgene stream being fed into the reactor through the remaining free space.

According to the invention the vaporous diamines are in a gaseous state and may optionally contain amounts of droplets of non-vaporized diamines (aerosol). Preferably the vaporous diamines do not contain droplets of non-vaporized diamines.

Those skilled in the art will recognize that the diamine-containing stream and the phosgene stream may also be exchanged, so that the phosgene stream is fed into the tube reactor through the n nozzles and the diamine-containing stream is fed into the tube reactor through the remaining free space.

Examples of suitable aliphatic diamines are mentioned e.g. in EP-A 0 289 840. Isophorone diamine (IPDA), hexamethylene diamine (HAD) and bis(p-aminocyclohexyl) methane being preferred.

Examples of suitable aromatic diamines are the pure isomers or isomer mixtures of diamino benzene, diamino toluene, diamino dimethyl benzene, diamino naphthaline and of diamino diphenyl methane. 2,4-/2,6-toluylene diamine mixtures with isomer ratios of 80/20 and 65/35 or the pure 2,4-toluylene diamine isomer are preferred.

Before carrying out the process according to the invention, the starting amines of formula (II) are fed into the reactor, in vapor form and heated to 200° C. to 600° C., preferably 250° C. to 450° C. and optionally rarefied with an inert gas such as $N_2$, He, Ar or with the vapors of an inert solvent e.g. aromatic hydrocarbons with or without halogen substitution.

The phosgene used for phosgenation is heated to a temperature of 200° C. to 600° C., preferably 250° C. to 450° C. before being fed into the reactor.

The diamine-containing stream is introduced centrally into the phosgene stream through a multi-nozzle consisting of n single nozzles, preferably of the same diameter $d_n$, the flow rate of the diamine-containing stream at the nozzle outlet being greater than the flow rate of the phosgene stream. The rate of the diamine-containing stream is preferably greater than the rate of the phosgene stream by a factor of at least 5–40.

The arrangement of the multi-nozzle varies preferably from n=2 to 9 individual nozzles of the same construction arranged in the form of a ring. Nozzles arranged in a ring having n=3 to 6 individual nozzles are preferred, n=6 is preferred in particular. Alternatively for example, arrangements of n-1 nozzles arranged in a ring around a centrally-arranged nozzle where n=4 to 8 are also possible. Multi-nozzles having 3 to 7 individual nozzles arranged in a ring and a central nozzle, preferably 5 or 6 individual nozzles arranged in a ring and a central nozzle, are preferred. To optimize intermixing and to avoid back-flow, the diameter of the central nozzle may differ from the diameter of the n individual nozzles arranged in a ring. The arrangement of the n individual nozzles of the multi-nozzle along a circular line is preferably to be selected in such a way that the ratio of the area of the circular ring between the circular line and the outer wall of the reactor to the area of the circle defined by the circular line moves in the range of 0.5 to 3, in particular in the range of 1 to 2.5.

From the diameter of the individual nozzles, a fictitious diameter $d_{fictitious}$ according to the formula $$d_{fictitious} = \sqrt{n \cdot d_n^2}$$

can be calculated, $d_n$, being the diameter of the n individual nozzles of the same construction. The fictitious diameter $d_{fictitious}$ is preferably in the range of 5% to 45% of the diameter D of the tube reactor.

When carrying out the process according to the invention, the pressure in the feed lines to the reaction chamber for the phosgene stream and the diamine-containing stream is preferably 200 mbar to 3000 mbar and at the outlet of the reaction chamber it is preferably 150 mbar to 2000 mbar, a flow rate inside the reaction chamber of at least 1 m/s, preferably at least 3 m/s and more preferably 5 m/s to 120 m/s being guaranteed by maintaining a suitable differential pressure. Under these pre-conditions turbulent flow conditions generally prevail inside the reaction chamber.

As shown in FIG. 1, reactor 1 is made of a case 10 in which the tube reactor 2 is fixed. The gaseous diamine-containing stream E1, produced by evaporation, is fed through the central nozzle 3 into the reaction chamber 8 of the tube reactor 2. The phosgene stream E2 is fed through the annular space 4 into the reaction chamber 8. Directly after the outlet 9 from the central nozzle 3, the diamine-containing stream E1 and the phosgene stream E2 are mixed and react to form the desired diisocyanate and undesirable by-products.

Figure 2:
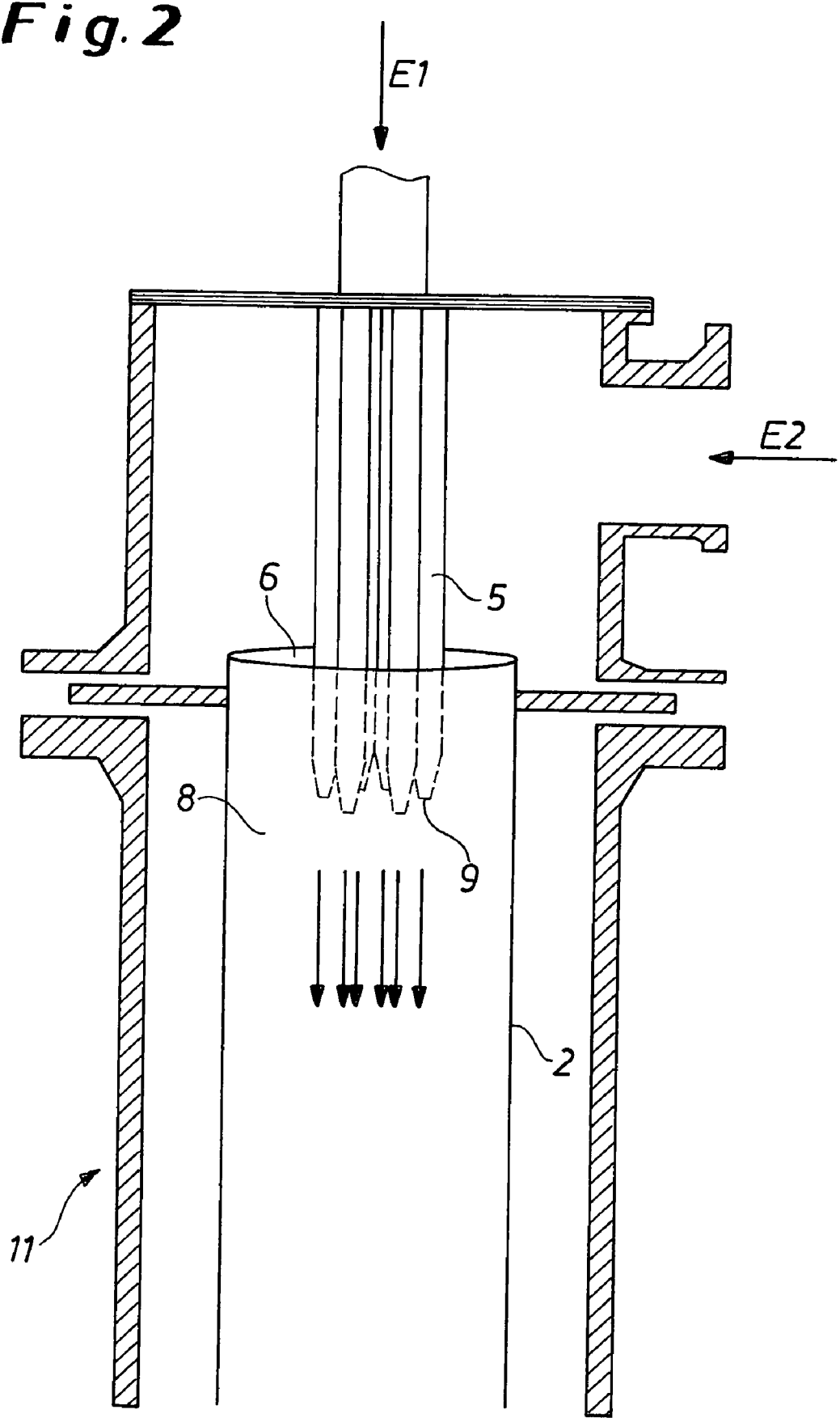
FIG. 2 illustrates a tube reactor with 6 individual nozzles arranged on a circular line.

FIG. 2 illustrates another reactor 11, in which the gaseous diamine-containing stream E1 is distributed amongst n=6 individual nozzles 5 and flows from the 6 individual nozzles 5 into the reaction chamber 8. The phosgene stream E2 is fed parallel to the nozzles through the remaining free space 6 into the reaction chamber 8. The free space 6 is the space in the inlet area of the tube reactor 2 not taken up by the individual nozzles 5. Mixing and reaction of the diamine and phosgene take place directly after the outlet 9 of the diamine from the individual nozzles 5.

FIG. 3 provides a front view of the tube reactor 2 of FIG. 2. The n=6 individual nozzles 5 are arranged about a circular line 7, the diameter of each individual nozzle is given by $d_n$ and the diameter of the tube reactor by D. The free space 6 extends over the whole area of cross-section of the tube reactor 2, and is thus both between the circular line 7 and the outer wall of the tube reactor 2 and also inside the area defined by the circular line 7.

EXAMPLES

Comparative Example C1

In a combined mixing and reaction tube 2 according to FIG. 1, followed by an isocyanate condensation step which, in turn, was followed by working-up of the isocyanate (according to the prior art), an isomer mixture of 2,4-/2,6-toluylene diamine (TDA 80/20), phosgene and nitrogen in a molar ratio of 1:6:0.2 flowed continuously through a centrally-arranged single nozzle 3, which protruded into the reaction tube 2. The educts were evaporated separately from each other in pure form and superheated to a temperature of 340–370° C. in a preliminary heat exchanger step. A mixture of nitrogen and TDA (E1) flowed through the single nozzle 3, phosgene (E2) in the annular space 4 between tube reactor 2 and single nozzle 3. The ratio of the area of cross-section of the reaction chamber to the single nozzle was 192:1. The pressure in the reaction zone was 1.5 bar. The flow rate of the reaction mixture after the single nozzle 3 in the reaction chamber 8 was about 1.6 m/s. After a residence time of about 2.5 sec in the gas phase, the reaction product 2,4-/2,6-toluene diisocyanate (TDI 80/20) was condensed at the end of reaction tube 2 by injection cooling, and was then used for dephosgenation and work-up by distillation of the phosgene-containing crude TDI (condensate) or for purifying the by-product hydrogen chloride (vapor). The yield of TDI was measured on samples of the phosgene-containing crude TDI at various times during the trial, followed by separation by distillation and quantitative measurement of polymeric by-products and also gas chromatographic measurement of the TDI content of the distillate in the laboratory. The TDI yield was max. 98.3% of theoretical in relation to the TDA used. The selected arrangement allowed very even operation. After controlled termination of the reaction and checking of the reactor for contamination after 96 h operation, unevenly-distributed areas of contamination were visible in the upper reaction area Such areas of contamination can have a technically detrimental effect on flow during longer periods of continuous operation and increasingly result in deposits on the wall of the reaction tube 2.

Example 2

In a combined mixing and reaction tube 2 according to FIG. 2, followed by an isocyanate condensation step which, in turn, was followed by work-up of the isocyanate, an isomer mixture of 2,4-/2,6 toluene diamine (TDA 80/20), phosgene and nitrogen in a molar ratio of 1:6:0.2 flowed continuously through a multi-nozzle having 6 individual nozzles 5, arranged in a circle, which protrudes into the reaction tube 2. The educts were evaporated separately from each other, in pure form, and superheated to a temperature of 340–370° C. in a preliminary heat exchanger step. A mixture of nitrogen and TDA (E1) flowed though the 6 individual nozzles 5, arranged in a circle, phosgene (E2) flowed in the remaining free space 6 around the individual nozzles 5. The ratio of the area of cross-section of reaction chamber 8 to the total area of the 6 individual nozzles 5 was (as with example 1) 192:1. The pressure in the reaction zone was 1.5 bar. The flow rate of the reaction mixture after the multi-nozzle was about 1.6 m/s. After a residence time of about 2.5 sec in the gas phase, the reaction product 2,4-/2,6-toluylene diisocyanate (TDI 80/20) was condensed by injection cooling at the end of the reaction tube 2, and was then used for de-phosgenation and work up by distillation of the phosgene-containing crude TDI (condensate) and purification of the by-product hydrogen chloride (vapor). The yield of TDI was measured on samples of the phosgene-containing crude TDI at various times during the trial, followed by separation by distillation and quantitative measurement of polymeric by-products and also gas-chromatographic measurement of the TDI content of the distillate in the laboratory. The TDI yield was max. 98.4% of theoretical in relation to the TDA used. The selected arrangement allowed for very even operation. After controlled termination of the reaction and checking of the reactor for contamination after 114 h operation, only slight, evenly-distributed areas of contamination were detected in the upper reaction area, which would not present any disadvantages for flow during longer periods of continuous operation.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the manufacture of a diisocyanate of the formula (I)

OCN—R—NCO   (I), wherein
R represents a (cyclo-)aliphatic or aromatic hydrocarbon group having up to 15 carbon atoms, provided that at least two carbon atoms are arranged between the two NCO groups,
by phosgenation of the corresponding vaporous diamine of the formula (II)

$H_2N$—R'—$NH_2$   (II), wherein
R' represents a (cyclo-)aliphatic or aromatic hydrocarbon group having up to 15, provided that at least two carbon atoms are arranged between the two amino groups,
in which the vaporous diamine, optionally rarefied with an inert gas or with the vapors of an inert solvent, and phosgene are heated separately to temperatures of from about 2000° C. to about 600° C., mixed and reacted in a tube reactor having a number n≧2 of nozzles directed parallel to the axis of the tube reactor arranged in the tube reactor, the diamine-containing stream being fed into the tube reactor through the n nozzles and the phosgene stream being fed into the tube reactor through remaining free space.

2. A process for the manufacture of a diisocyanate of the formula (I)

OCNR—R—NCO     (I).

wherein
R represents a (cyclo-)aliphatic or aromatic hydrocarbon group having up to 15 carbon atoms, provided that at least two carbon atoms are arranged between the two NCO groups,
by phosgenation of the corresponding vaporous diamine of the formula (II)

H$_2$N—R'—NH$_2$     (II).

wherein
R' represents a (cyclo-)aliphatic or aromatic hydrocarbon group having un to 15, provided that at least two carbon atoms are arranged between the two amino groups, in which the vaporous diamine, optionally rarefied with an inert gas or with the vapors of an inert solvent, and phosgene are heated separately to temperatures of from about 200° C. to about 600° C. mixed and reacted in a tube reactor having a number n≧2 of nozzles directed parallel to the axis of the tube reactor arranged in the tube reactor , the phosgene stream being fed into the tube reactor through n nozzles and the diamine-containing stream being fed into the tube reactor through the free space.

3. The process according to claim 1, wherein the diamine of formula (II) is chosen from isophorone diamine (IPDA) or hexamethylene diamine (HDA) and bis(p-aminocyclohexyl)-methane.

4. The process according to claim 1, wherein the diamine of formula (II) is a mixture of 2,4-/2,6-toluene diamine.

5. The process according to claim 4, wherein the diamine of formula (II) is chosen from 2,4-/2,6-toluylene diamine mixtures of isomer ratios of about 80/20 and about 65/35 and pure 2,4-toluylene diamine isomers.

6. The process according to claim 1, wherein R' represents a (cyclo-) aliphatic or aromatic hydrocarbon group having 4 to 13 carbon atoms.

7. The process according to claim 1, wherein the vaporous diamine, optionally rarefied with an inert gas or with the vapors of an inert solvent, and phosgene are heated separately to temperatures of from about 250° C. to about 450° C.

8. The process according to claim 2, wherein the diamine of formula (II) is chosen from isophorone diamine (IPDA) or hexamethylene diamine (HDA) and bis(p-aminocyclohexyl)-methane.

9. The process according to claim 2, wherein the diamine of formula (II) is a mixture of 2,4-/2,6-toluene diamine.

10. The process according to claim 9, wherein the diamine of formula (II) is chosen from 2,4-/2,6-toluylene diamine mixtures of isomer ratios of about 80/20 and about 65/35 and pure 2,4-toluylene diamine isomers.

11. The process according to claim 2, wherein R' represents a (cyclo-) aliphatic or aromatic hydrocarbon group having 4 to 13 carbon atoms.

12. The process according to claim 2, wherein the vaporous diamine, optionally rarefied with an inert gas or with the vapors of an inert solvent, and phosgene are heated separately to temperatures of from about 250° C. to about 450° C.

* * * * *